US00PP20057P2

(12) United States Plant Patent
Beller

(10) Patent No.: US PP20,057 P2
(45) Date of Patent: Jun. 2, 2009

(54) APPLE TREE NAMED 'BELLER'

(50) Latin Name: *Malus domestica*
Varietal Denomination: Beller

(75) Inventor: Ray Beller, Malott, WA (US)

(73) Assignee: Karen Beller, Malott, WA (US)

( * ) Notice: Subject to any disclaimer, the term of this patent is extended or adjusted under 35 U.S.C. 154(b) by 0 days.

(21) Appl. No.: 12/074,125

(22) Filed: Feb. 29, 2008

(51) Int. Cl.
*A01H 5/00* (2006.01)

(52) U.S. Cl. ..... Plt./161
(58) Field of Classification Search ..... Plt./161
See application file for complete search history.

*Primary Examiner*—Kent L Bell
(74) *Attorney, Agent, or Firm*—Wells St. John P.S.

(57) ABSTRACT

A new and distinct variety of apple tree is described and which is characterized as to novelty by producing an attractively colored apple which is mature for harvesting and shipment approximately October 20$^{th}$ under the ecological conditions prevailing in Malott, Wash.

2 Drawing Sheets

BACKGROUND OF THE NEW VARIETY

The present invention relates to a new and distinct variety of apple tree, '*Malus domestica Borkh*' and which has been denominated varietally hereinafter as 'Beller', and more particularly to an apple tree which bears an attractively colored substantially uniform fruit which has a sweet-tart flavor, excellent storage ability, a fine grained flesh, and which is further ripe for harvesting and shipment about Oct. 20, 2007 under the ecological conditions prevailing near Malott, Wash.

ORIGIN AND ASEXUAL REPRODUCTION

It has long been recognized that an important factor contributing to the success of any new variety of apple tree bearing fruit for the fresh market is its respective harvesting date in relative comparison to other varieties bearing similar fruit in the same season. Similarly, other significant factors effecting the commercial viability of any new strain of apple relates to its appearance as well as its storage characteristics as reflected by such pomological characteristics as a starch level, fruit pressure, brix and other similar characteristics.

The new variety 'Beller' is noteworthy in producing an attractively colored fruit which is ripe for harvesting and shipment approximately Oct. 20, 2007 under the ecological conditions prevailing near Malott, Wash. Further, this new variety of apple tree produces fruit which have excellent storage characteristics in relative comparison to other varieties to which it is most closely similar.

The new variety of apple tree as described herein was discovered within the cultivated region of an apple orchard owned by the inventor. In this regard, the orchard comprised a block of 'Red Delicious' (unpatented) apple trees which included at least one row of 'Golden Delicious' (unpatented) trees growing therein. This orchard had previously been removed by the inventor in 1979 in anticipation of replanting. While the orchard was laying fallow, the inventor, in 1981, discovered a chance seedling in the former 'Golden Delicious' row of apple trees that had been growing in the orchard. This chance seedling was marked for subsequent observation. The inventor thereafter studied the tree and the fruit produced therefrom until 1986. In 1986, the inventor removed scion wood from the chance seedling and grafted it into five test trees that were then growing at the same orchard. These test trees were observed until 1990. During this time period, the inventor diligently compared and contrasted the first asexually reproduced trees with that of the original chance seedling. In 1990, the inventor again removed scion wood from the chance seedling and grafted 50 more trees for further observation. In addition to the foregoing, further asexual reproductions took place in 1994 within a commercial nursery located in north central Washington. None of the foregoing test trees have ever been sold, or offered for sale to the public.

All the test trees, noted above, have been studied and observed by the inventor, and it has been determined that the same desirable characteristics observed in the original chance seedling were expressed in these same test trees. It has been confirmed through these observations that the earlier asexual reproductions, as noted above, resulted in apple trees which produce fruit which possess the same distinctive characteristics as the original chance seedling.

SUMMARY OF THE VARIETY

The 'Beller' apple tree is characterized principally as to novelty by producing an attractively colored fruit which is ripe for harvesting and shipment approximately Oct. 20, 2007 under the ecological conditions in north central Washington. In contrast to the varieties with which it is most closely similar to, the present variety does not resemble either the fruit produced by the 'Red Delicious' (unpatented) or 'Golden Delicious' (unpatented) apple trees, both of which were previously grown in the same orchard. In this regard, the 'Red Delicious' and 'Golden Delicious' (both unpatented) apple trees produce fruit which are conic in shape, and have prominent lobes on the apex thereof. In contrast, the apple tree 'Beller' produces fruit which is round in shape with no appearance of lobes in the basin region. Further, the 'Beller' apple tree produces fruit which mature much later in the season (at least two weeks) than either the fruit produced by the 'Red Delicious' or 'Golden Delicious' (both unpatented) trees growing under the same ecological conditions. In addition to the foregoing, the 'Beller' apple tree produces a bloom on unpolished fruit which is unlike either of the fruit produced by the 'Red Delicious' or 'Golden Delicious' apple trees when grown in the same geographical location and under substantially similar horticultural practices.

Figure 1:
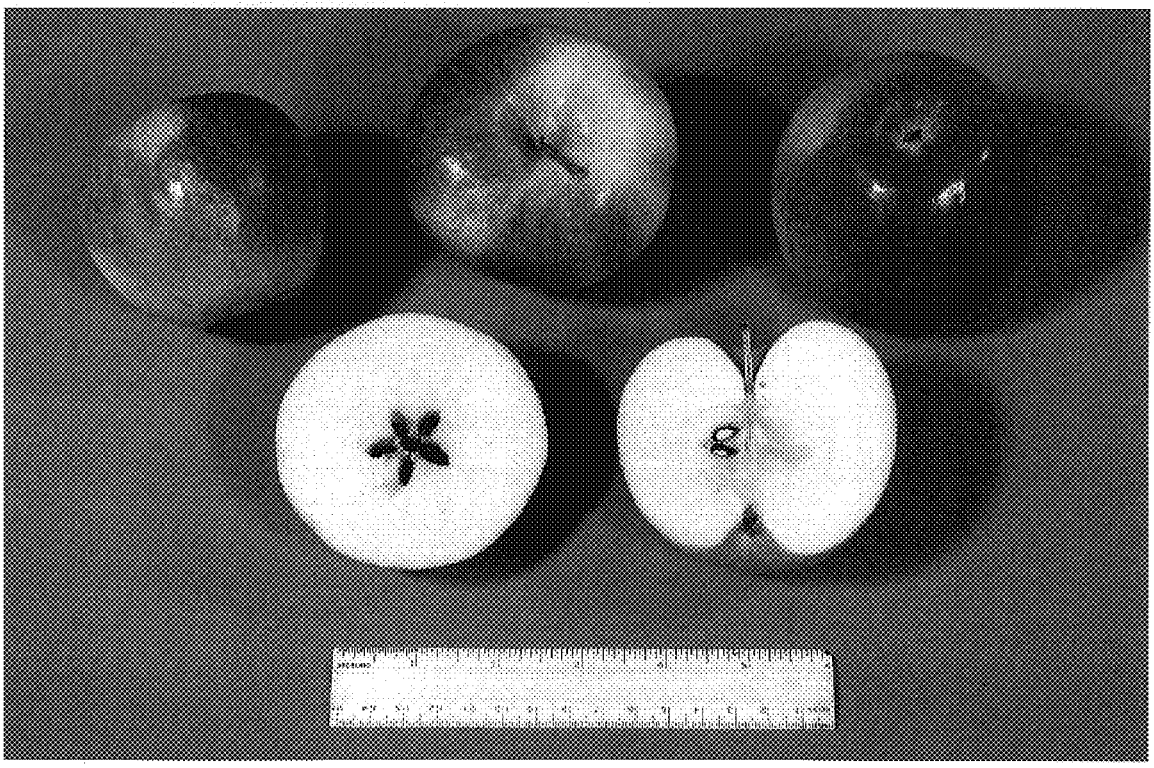
FIG. 1 illustrates several fruit of the present variety sufficiently matured for harvesting and shipment and two fruit of the present variety one of which is dissected in the axial plane to show the flesh and seed characteristics thereof, and the other apple dissected in a plane substantially transverse to the axial plane.
Figure 2:
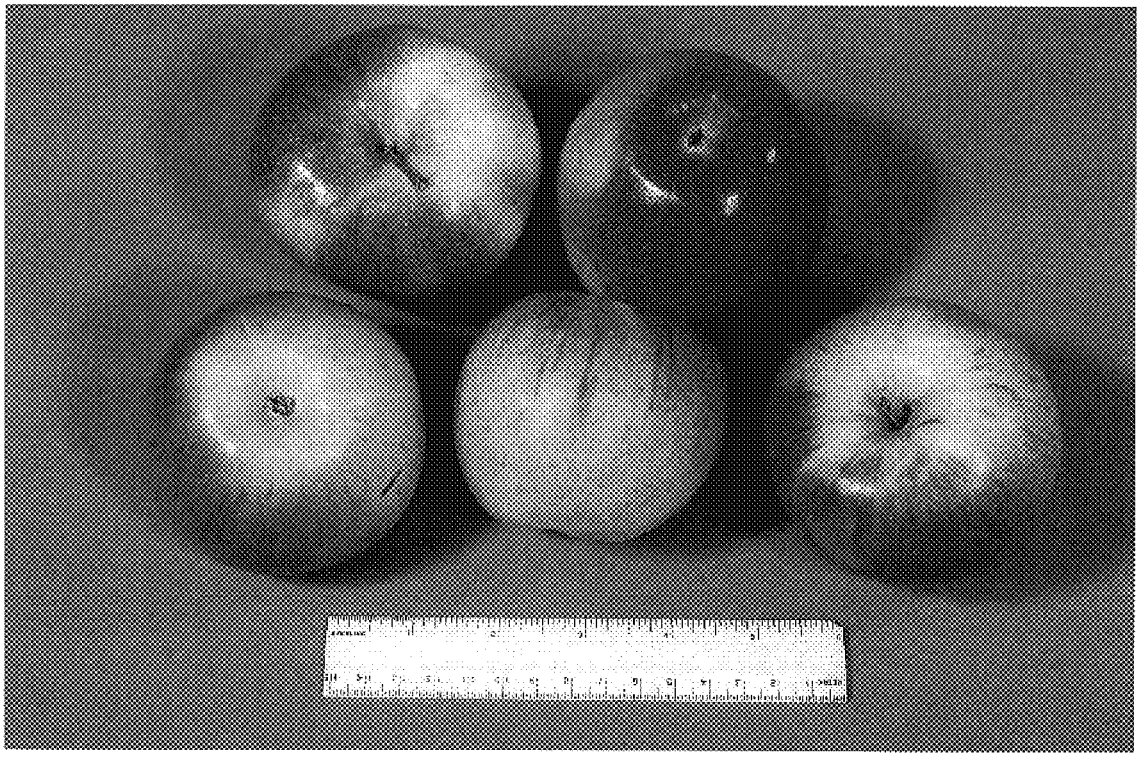
FIG. 2 shows several fruit of the present variety sufficiently matured for harvesting and shipment in various orientations, so as to show the skin coloration and characteristics thereof.

The colors in the enclosed photographs are as nearly true as is reasonably possible in color photographs of this type. However, due to chemical development, processing and printing, the fruit color depicted in these photographs may or may not be accurate when compared to the actual botanical specimens. For this reason, future color references should be made to the color plates provided in the Munsell Book of Color, published by Kollmorgen Instruments Corp. of New Windsor, N.Y. Common color names are also used, occasionally.

NOT A COMMERCIAL WARRANTY

The following detailed description has been prepared to solely comply with the provisions of 35 USC §112, and does not constitute a commercial warranty (either expressed or implied) that the present variety will in the future display the botanical, pomological or other characteristics as set forth hereinafter. Therefore, this disclosure may not be relied upon to support any future legal claims including, without limitation, any claims relating to the breach of warranty of merchantability or fitness for any particular purpose which is directed, in whole or in part, to the present variety.

DETAILED DESCRIPTION

Tree:

*Size.*—Generally — The tree as described hereinafter is a second generation asexually reproduced tree which was planted in 1986. As a general matter, the present tree is average in size and form as compared to other apple cultivars growing under similar ecological conditions in north central Washington.

*Height.*—About 2.5 meters to about 4 meters.

*Width.*—About 2 meters to about 2.5 meters.

*Overall shape.*—Considered upright to upright spreading.

*Vigor.*—Considered average, and producing about 15–25 inches of annual growth per year.

*Productivity.*—Annually Productive. No tendency to biennial bearing was observed.

*Chilling requirements.*—Unknown.

Trunk:

*Generally.*—The trunk has a diameter of about 8 cm. when measured at a distance of about 0.5 meters from the surface of the ground in 2007.

*Bark texture.*—Smooth and indistinctive on young trees, and becoming increasingly rough with advancing age.

*Bark color.*—Yellow-brown (7.5 YR 6/10) to brown (7.5 YR 4/8). The trunk characteristics and bark color are not distinctive of the present variety.

Branches:

*Branching habit.*—Upright to upright spreading.

*Crotch angle.*—About 30 degrees to about 60 degrees when measured from the trunk at emergence.

*Branches.*—Size and texture — Quite similar to that produced by the 'Golden Delicious' apple tree (unpatented) growing in the same geographical location. The branching habit and bark texture of the branches is otherwise non-distinctive.

*Branch color.*—2 year fruiting branches, medium brown (10 YR 4/4).

*Branch pubescence.*—1 year shoots — A fine colorless pubescence exists on such branches. This pubescence disappears on older wood.

*Branch lenticels.*—Considered sparse and inconspicuous. This does not appear to be a distinctive characteristic of the present tree.

*Internodes.*—When measured on 1 year old shoots, about 15–20 mm.

Leaves:

*Generally.*—Considered average as compared to other varieties.

*Shape.*—Considered broad, and oblong, and being acute to acuminate.

*Base shape.*—Obtuse.

*Mid-vein color.*—Light, yellow-green (10 Y 8.5/6).

*Venation pattern.*—The leaves display alternate, lateral venation.

*Leaf length.*—About 75 mm. to about 90 mm.

*Leaf width.*—About 53 mm. to about 65 mm.

*Petiole length.*—About 20 mm. to about 35 mm.

*Marginal form.*—Considered finely crenate.

*Leaf tip.*—Shape — Acuminate.

*Leaf stipules.*—1 year old shoots — Generally lacking, however, when stipules are present, they appear in pairs and are considered very small and narrowly pointed. The leaf stipules are about 5 mm. in length, and about 1 mm. in width.

*Leaf surface texture.*—Upper surface — Glabrous.

*Leaf surface texture.*—Lower surface — Finely pubescent.

*Leaf color.*—Upper surface — Green (5 GY 4/8).

*Leaf color.*—Lower surface — Grey-green (5 GY 5/4).

*Petiole color.*—Purple (5 R 5/6).

*Pubescence color.*—Grey (10 RP 8/2).

Flowers:

*Bloom time.*—Considered average as compared to other apple tree varieties growing in north central Washington. The present variety had an observed first bloom date of April 20 in 2007, and achieved full bloom on Apr. 27, 2007.

*Bloom duration.*—Approximately 14 days under the ecological conditions prevailing in north central Washington.

*Buds.*—Shape — Considered round and occasionally oval.

*Buds.*—Length — About 10 mm.

*Buds.*—Diameter — Approximately 7 mm.

*Flower size.*—When fully opened, the flowers are considered medium to large for the species, about 36 mm. to 48 mm. in diameter.

*Flower color.*—The flowers are pink when it is in the bud stage (5 RP 6/10). The flower is near white (2.5

RP 9/2) when fully opened. This white color is not distinctive of the variety.

*Flower petals.*—Numbers — 5. Length — 25 mm.; width 19 mm. (average).

*Flower petals.*—Shape — Rounded at the apex, and obtuse at the base.

*Flower petal margins.*—Considered smooth.

*Flower petal.*—Texture — smooth.

*Flower petals.*—Position — The flower petals at the margins are either touching or slightly overlapping.

*Stamens.*—Arrangement — appearing typically in a single row.

*Stamens.*—Number — 16.

*Stamens.*—Length — About 7 mm.

*Anthers.*—Color — Yellow (5 Y 8.5/10).

*Pistil.*—Length — Considered average, about 8 mm.

*Pistil.*—Shape — Branched at the tip to form 5 stigma elements.

*Sepals.*—Numbers — 5.

*Sepals.*—Length — About 6 mm.

*Sepals.*—Width — As measured at the base, about 4 mm.

*Sepals.*—Surface texture — Pubescent.

*Sepals.*—Shape — Tapering to a point and recurved downward; margins smooth.

*Sepals.*—Color — Grey-green (10 Y 8/4).

*Peduncle.*—Length — About 15 mm.–20 mm.

*Peduncle.*—Diameter — About 1 mm.–2 mm.

*Peduncle.*—Color — Grey-green (10 Y 8/4).

*Flower fragrance.*—Light, and typical of apple trees. This characteristic is not distinctive of the present variety, however.

*Pollination requirements.*—Presently unknown. However, the variety is assumed to be a compatible diploid.

Fruit:

*Maturity when described.*—Ripe for harvesting and shipment, about Oct. 20, 2007 under the ecological conditions prevailing near Malott, Wash.

*Fruit firmness.*—About 18.26 pounds as determined by a Taylor-Magness pressure tester.

*Brix.*—About 16.70.

*Malic acid content.*—(Titration) — About 0.5 percent.

*Starch index.*—On a scale from 1–6, about 3.95.

*Fruit size.*—Generally — Considered medium and uniform. The average cross-sectional diameter of the fruit is about 75–85 mm. Average axial diameter of the fruit is about 70–75 mm. Average fruit weight 225 grams.

*Fruit form.*—Round and symmetrical. This is in stark contrast to the fruit produced by the 'Red Delicious' (unpatented) and 'Golden Delicious' apple trees which grow in the vicinity. The fruit produced by the present tree has no ribbing and no lobes are evident on the calyx end. This lobing is, of course, a characteristic of the fruit produced by both the 'Golden Delicious' (unpatented) and 'Red Delicious' (unpatented) apple trees.

*Stem cavity.*—About 35–40 mm. wide when measured shoulder to shoulder.

*Stem cavity.*—Depth — 15 mm.

*Stem cavity.*—Shape — Acute to obtuse.

*Stem cavity.*—Surface texture — Smooth, with no evidence of russet.

*Stem.*—Length — Considered average, about 15 to 25 mm.

*Stem.*—Thickness — About 2–3 mm. Stem Color. — Reddish Purple (10 RP 3/6).

*Basin cavity.*—Width — About 35 mm. to about 40 mm.

*Basin cavity.*—Depth — About 15 mm.

*Basin cavity.*—Surface Texture — Smooth.

*Basin cavity.*—Shape — Acuminate to acute. No lobes are evident.

*Carpals.*—Size — Considered medium to large for the species; Average Length — 25 mm.; Width — 25 mm.

*Carpals.*—Number 5.

*Carpals.*—Form — Generally open with the seeds loosely attached.

*Fruit skin.*—Generally — considered thin, tender, dull in appearance and having a light bloom. The fruit skin does not appear prone to russet or cracking.

*Lenticels.*—Size — Considered small. About 1 mm. in diameter.

*Lenticels.*—Numbers — About 1–2 lenticels are found per square centimeter of fruit skin.

*Lenticels.*—Color — Considered a slightly off-white color. This color is not distinctive of the variety, however.

*Fruit skin color.*—Considered bi-colored and a combination of both striped and blushed red colors which are present and cover 50% to over 80% of the fruit surface.

*Ground color.*—Yellow (2.5 Y 8.5/12).

*Overcolor.*—Dark purple red stripes (5 R 3/10) are present. These stripes are of variable length and width over a red blush which is characterized as (5 R 5/10).

*Russet.*—Absent on the present variety.

*Flesh color and texture.*—Light cream (7.5 Y 9/2); and considered finely grained.

*Flesh flavor.*—Considered sweet as compared to other varieties.

*Flesh aroma.*—Present, but considered low for the variety.

*Core.*—Shape — The bundle area is considered round. The core has a width of about 28 mm. to about 45 mm.

*Core.*—Length — About 38 mm.

*Numbers of bundles.*—10.

*Core lines.*—Generally — Considered prominent.

*Locules.*—Position — Open.

*Calyx tube.*—Length — About 5 mm.

*Calyx tube.*—Position — Closed.

*Seed numbers.*—Generally one seed is found per cell.

*Seeds.*—Shape — Obovate.

*Seeds.*—Color — Dark brown (7.5 YR 3/6).

*Seeds.*—Length — About 7 mm.

*Seeds.*—Width — About 5 mm.

*Keeping quality.*—Considered average for the variety, about 3–4 months under normal storage conditions.

*Fruit usage.*—Primarily a fresh eating, dessert type apple.

*Disease resistance.*—Unknown.

Although the new variety of apple tree herein denominated as 'Beller' possesses the described characteristics when grown under the ecological conditions prevailing near Malott, Wash. it is to be understood that variations of the usual magnitude and characteristics incident to changes in growing conditions, fertilizing, pruning and pest control are to be expected.

Having thus described and illustrated my new variety of apple tree, what I claim is new, and desire to secure by plant letters patent is:

1. A new and distinct variety of apple tree as substantially illustrated and described and which is characterized principally as to novelty by producing an attractively colored apple which is mature for harvesting and shipment approximately October $20^{th}$ under the ecological conditions prevailing in north central Washington.

* * * * *